(12) United States Patent
Gradon et al.

(10) Patent No.: US 10,463,828 B2
(45) Date of Patent: Nov. 5, 2019

(54) BREATHING ASSISTANCE APPARATUS (75) Inventors: Lewis George Gradon, Auckland (NZ); Alastair Edwin McAuley, Auckland (NZ); Chris Earl Nightingale, Auckland (NZ); Ivan Milivojevic, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 235 days.

(21) Appl. No.: 10/487,518

(22) PCT Filed: Oct. 10, 2002

(86) PCT No.: PCT/NZ02/00212
§ 371 (c)(1),
(2), (4) Date: Jul. 29, 2004

(87) PCT Pub. No.: WO03/030978
PCT Pub. Date: Apr. 17, 2003

(65) Prior Publication Data
US 2004/0255950 A1    Dec. 23, 2004

(30) Foreign Application Priority Data
Oct. 10, 2001 (NZ) ........................................ 514750

(51) Int. Cl.
*A62B 18/08* (2006.01)
*A62B 18/02* (2006.01)
(Continued)

(52) U.S. Cl.
CPC .... *A61M 16/1075* (2013.01); *A61M 16/0069* (2014.02); *A61M 16/06* (2013.01);
(Continued)

(58) Field of Classification Search
CPC ... A61B 18/08; A61M 16/06; A61M 16/0633; A61M 16/0644; A61M 16/065;
(Continued)

(56) References Cited

U.S. PATENT DOCUMENTS 2,563,710 A * 8/1951 Epstein ................. F23L 17/02
454/36
4,378,011 A * 3/1983 Warncke et al. ........ 128/204.26
(Continued)

FOREIGN PATENT DOCUMENTS

CA   2 470 671 A1 * 2/1998
CA   2 470 671 A1 * 5/1998
(Continued)

OTHER PUBLICATIONS

United States Publication No. US2002/0026934 Published on Mar. 7, 2002; Inventor: Lithgow et al.

*Primary Examiner* — Kari K Rodriquez
*Assistant Examiner* — Camtu T Nguyen
(74) *Attorney, Agent, or Firm* — Knobbe Martens Olson & Bear LLP (57) ABSTRACT

A user interface for delivering CPAP includes a forehead adapted with a deformable attachment between the interface and the support. In the preferred embodiment the interface is a mask which substantially seals against the face of the user without substantial pressure thereto and delivers said gases to the nasal cavity and/or oral cavity and/or throat.

21 Claims, 6 Drawing Sheets

(51) Int. Cl.
   *A62B 7/10* (2006.01)
   *A61M 16/06* (2006.01)
   *A61M 16/10* (2006.01)
   *A61M 16/16* (2006.01)
   *A61M 16/00* (2006.01)

(52) U.S. Cl.
   CPC .... *A61M 16/0616* (2014.02); *A61M 16/0622* (2014.02); *A61M 16/0633* (2014.02); *A61M 16/0638* (2014.02); *A61M 16/109* (2014.02); *A61M 16/16* (2013.01); *A61M 16/0683* (2013.01)

(58) Field of Classification Search
   CPC ........ A61M 16/0655; A62B 9/04; A62B 7/00; A62B 7/02; A62B 7/04; A62B 7/06; A62B 7/08; A62B 7/10; A62B 7/12; A62B 7/14; A62B 9/00; A62B 9/003; A62B 9/006; A62B 9/02; A62B 9/025; A62B 9/027; A62B 9/06; A62B 18/00; A62B 18/02; A62B 18/025; A62B 18/04; A62B 18/06
   USPC ............ 128/207.11, 207.26, 207.13, 206.12, 128/206.27, 206.28, 206.29, 205.25, 128/205.29
   See application file for complete search history.

(56) References Cited

U.S. PATENT DOCUMENTS

| | | | |
|---|---|---|---|
| 5,243,971 A * | 9/1993 | Sullivan et al. | 128/205.25 |
| 5,259,377 A * | 11/1993 | Schroeder | 128/207.14 |
| 5,429,683 A * | 7/1995 | Le Mitouard | 128/206.24 |
| 5,542,128 A | 8/1996 | Lomas | |
| 5,558,089 A * | 9/1996 | Castiglione | A41D 13/1146 |
| | | | 128/203.29 |
| 5,558,090 A * | 9/1996 | James | 128/207.18 |
| 5,570,689 A | 11/1996 | Starr et al. | |
| 5,657,752 A * | 8/1997 | Landis | A61M 16/06 |
| | | | 128/201.28 |
| 5,806,727 A * | 9/1998 | Joseph | A47G 25/32 |
| | | | 223/85 |
| 5,904,278 A * | 5/1999 | Barlow | A47G 25/32 |
| | | | 223/85 |
| 5,941,245 A * | 8/1999 | Hannah | A62B 18/084 |
| | | | 128/201.22 |
| 6,112,746 A * | 9/2000 | Kwok et al. | 128/207.13 |
| 6,119,693 A * | 9/2000 | Kwok et al. | 128/207.11 |
| 6,192,886 B1 * | 2/2001 | Rudolph | A61M 16/06 |
| | | | 128/205.25 |
| 6,427,694 B1 * | 8/2002 | Hecker | A61M 16/06 |
| | | | 128/201.22 |
| 6,712,072 B1 * | 3/2004 | Lang | A61M 16/0683 |
| | | | 128/206.16 |
| 6,918,390 B2 * | 7/2005 | Lithgow et al. | 128/206.27 |
| 2004/0025882 A1 * | 2/2004 | Madaus et al. | 128/206.27 |
| 2004/0065328 A1 * | 4/2004 | Amarasinghe | A61M 16/0683 |
| | | | 128/206.27 |
| 2004/0112384 A1 * | 6/2004 | Lithgow et al. | 128/206.21 |
| 2006/0005840 A1 * | 1/2006 | Cannon | A61M 16/0683 |
| | | | 128/207.11 |
| 2007/0062537 A1 * | 3/2007 | Chiesa | A61M 16/06 |
| | | | 128/207.11 |
| 2007/0221226 A1 * | 9/2007 | Hansen | A61M 16/06 |
| | | | 128/206.21 |

FOREIGN PATENT DOCUMENTS

| | | |
|---|---|---|
| WO | WO 0057942 | 10/2000 |
| WO | WO 0078384 | 12/2000 |
| WO | WO 0100266 | 1/2001 |

* cited by examiner

BREATHING ASSISTANCE APPARATUS

FIELD OF INVENTION

This invention relates to patient interfaces particularly though not solely for use in delivering CPAP therapy to patients suffering from obstructive sleep apnoea (OSA).

BACKGROUND OF THE INVENTION

In the art of respiration devices, there are well known variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. Nos. 5,243,971 and 6,112,746 are examples of prior art attempts to improve the mask system. U.S. Pat. No. 5,570,689 and PCT publication No. WO 00/78384, and U.S. Pat. No. 6,119,693 are examples of attempts to improve the forehead rest.

SUMMARY OF THE INVENTION

It is an object of the present invention to attempt to provide a patient interface which goes some way to overcoming the abovementioned disadvantages in the prior art or which will at least provide the industry with a useful choice.

Accordingly in one aspect the present invention consists in a device for delivering a supply of gases to a user comprising:

a mask, in use in fluid communication with a supply of gases, said mask configured to in use substantially seal against the face of a user without substantial pressure there to an deliver said gases to the nasal cavity or oral cavity or both of a user, a forehead support adapted to in use rest on the forehead of a user, and a deformable attachment between said mask and said forehead support configured to allow alteration of the relative forward and backward position of said forehead support with respect to said user interface, and restrict lateral movement of said forehead support relative to said user interface, a said deformable attachment including a weakened section which is adapted to allow plastic deformation so that said forehead support may be configured to a certain angle relative to said user interface and will retain said angle in use when said device is in use.

Preferably said deformable attachment comprises a metal strap between said user interface and said forehead support.

Preferably said strap is at least in part encapsulated by a pliable material.

In another aspect the present invention consists in a respiratory system user interface comprising:

a mask, a forehead support, and a malleable insert extending between and coupling the forehead support and the mask, the insert facilitating anterior and posterior adjustment of the forehead support relative to the mask and restraining movement of the mask relative to the forehead support in a lateral direction. Preferably insert is a metal strip, the metal strip having a reduced thickness in an anterior direction to facilitate anterior and posterior adjustment and an increased thickness in a lateral direction to restrict lateral movement.

Preferably the insert is coated with a soft pliable material.

Preferably opposing ends of the insert are encapsulated in the mask and the forehead support respectively.

Preferably the forehead rest is pivotably coupled to the insert.

Preferably the insert has a region of reduced thickness adjacent the mask.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION

The present invention provides improvements in the delivery of CPAP therapy. In particular a patient interface is described which is quieter for the user to wear and reduces the side leakage as compared with the prior art. It will be appreciated that the patient interface as described in the preferred embodiment of the present invention can be used in respiratory care generally or with a ventilator but will now be described below with reference to use in a humidified CPAP system. It will also be appreciated that the present invention can be applied to any form of patient interface including, but not limited to, nasal masks, oral masks and mouthpieces.

Figure 1:
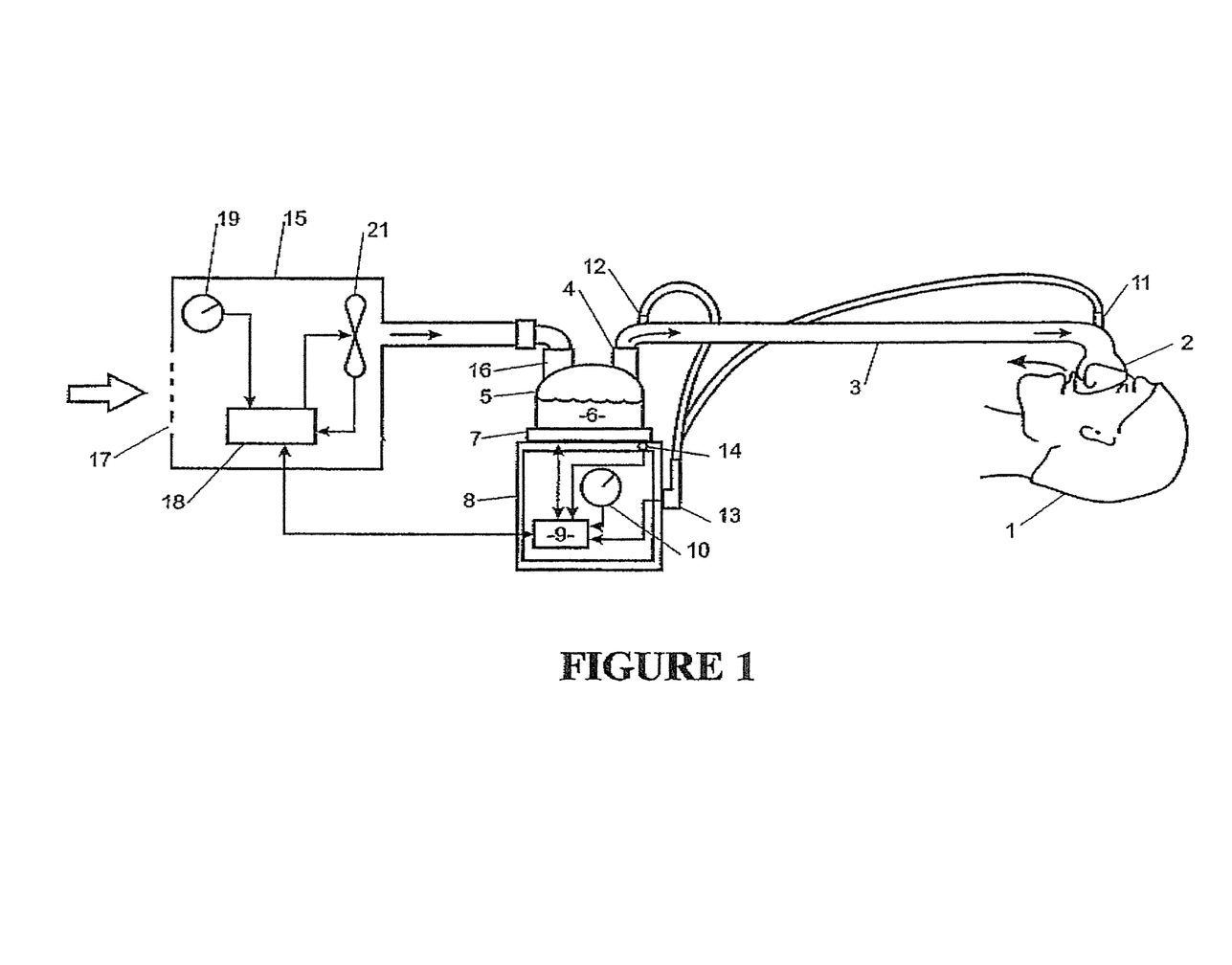
FIG. 1 is a block diagram of a humidified continuous positive airway pressure (system) as might be used in conjunction with the present invention.

With reference to FIG. 1 a humidified Continuous Positive Airway Pressure (CPAP) system is shown in which a patient 1 is receiving humidified and pressurised gases through a patient interface 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 1.

Blower 15 is provided with variable pressure regulating means or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Nasal Mask

Figure 2:
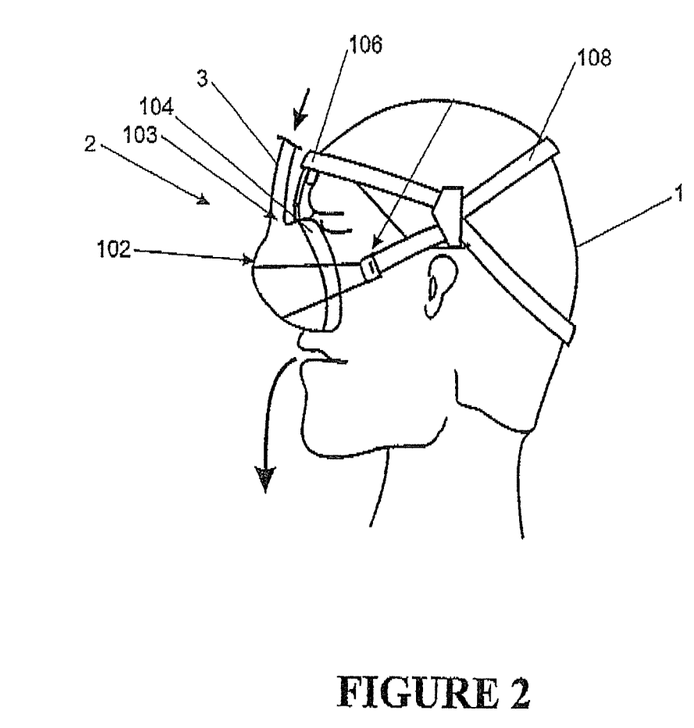
FIG. 2 is an illustration of the nasal mask in use according to the preferred embodiment of the present invention.

According to a first embodiment of the present invention the patient interface is shown in FIG. 2 as a mask. Alternatively it may be a nasal mask, full face mask, endotracheal tube, oral mask or mouthpiece, or nasal cannula The mask includes a hollow body 102 with an inlet 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Mask Cushion

Figure 3:
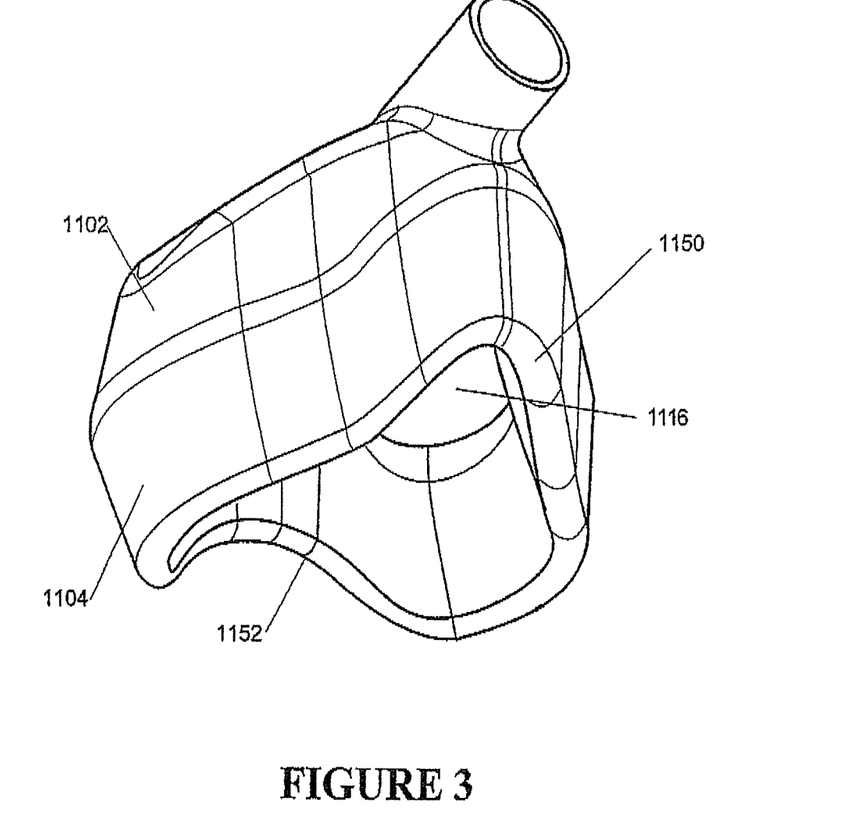
FIG. 3 shows a perspective view of the mask with cushion.
Figure 4:
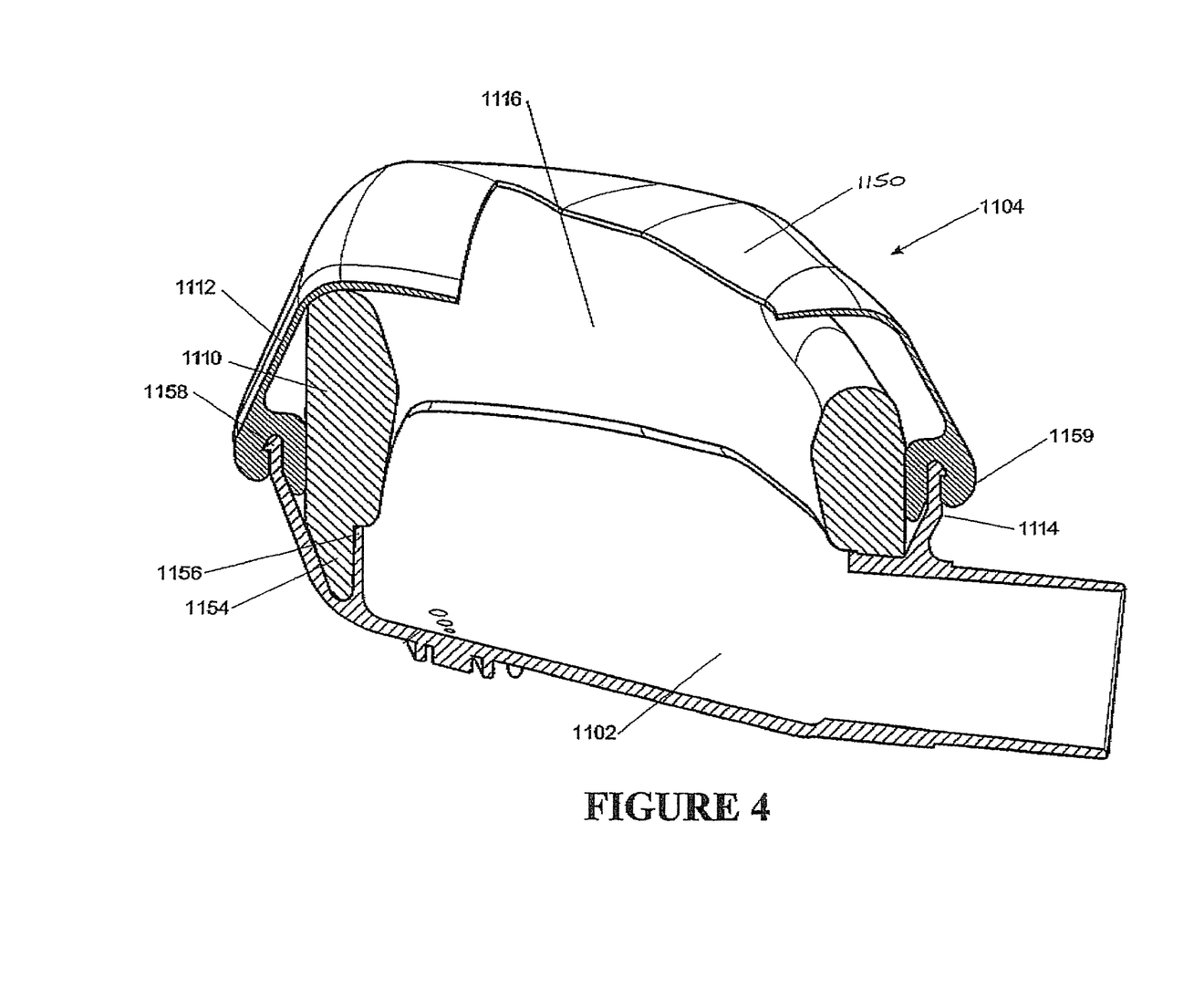
FIG. 4 is a cutaway view of the mask showing the cushion.

Referring now to FIGS. 3 and 4 in particular, the mask cushion 1104 is provided around the periphery of the nasal mask 1102 to provide an effective seal onto the face of the user to prevent leakage. The mask cushion 1104 is shaped to approximately follow the contours of a patient's face. The mask cushion 104 will deform when pressure is applied by the headgear 1108 to adapt to the individual contours of any particular user. In particular, there is an indented section 1150 intended to fit over the bridge of the user's nose as well as a less indented section 1152 to seal around the section beneath the nose and above the upper lip.

In FIG. 4 we see that the mask cushion 1104 is composed of a inner foam cushion 1110 covered by an outer sealing sheath 1112. The inner cushion 1110 is constructed of a resilient material for example polyurethane foam, to distribute the pressure evenly along the seal around the user's face. The inner cushion 1110 is located around the outer periphery 1114 of the open face 1116 of the hollow body 1102. Similarly the outer sheath 1112 may be commonly attached at its base 1113 to the periphery 1114 and loosely covers over the top of the inner cushion 1110.

In the preferred embodiment shown in FIGS. 3-6 the bottom of the inner cushion 1110 fits into a generally triangular cavity 1154 in the hollow body 1102. The cavity 1154 is formed from a flange 1156 running mid-way around the interior of the hollow body.

Figure 5:
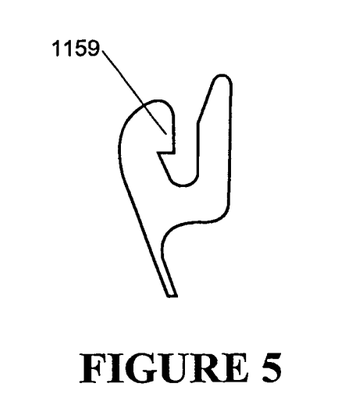
FIG. 5 is a cutaway view of the periphery of the outer membrane.
Figure 6:
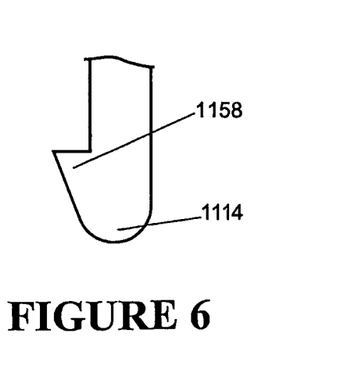
FIG. 6 is a cutaway view of the periphery of the mask body portion.

The outer sheath 1112 fits in place over the cushion 1110, holding it in place. The sheath 1112 is secured by a snap-fit to the periphery 1114 of the hollow body. In FIGS. 5-6 the periphery 1114 is shown including an outer bead 1158. The sheath 1112 includes a matching bead 1159, whereby once stretched around the periphery, the two beads engage to hold the sheath in place.

Forehead Rest

Figure 7:
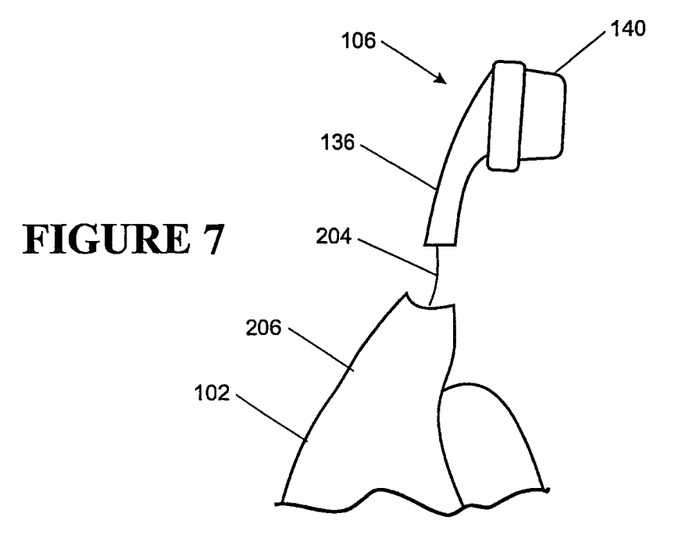
FIG. 7 is a side view of the forehead rest in isolation.

In the preferred embodiment of the present invention the interface includes a forehead rest 106 (seen in FIGS. 2 and 7). The attachment of the forehead rest 106 to the hollow body 102 effectively allows the forehead rest 106 angle to be adjusted in relation to the user but with no lateral movement.

At a T-section 142 at the top end (around the user's forehead) of the bridge member 136 harnessing slots 138 are provided which allow straps from the headgear to be inserted to secure the mask to the headgear. For the user's comfort one or more resilient cushions 140 are provided underneath the T-section 142 at the top end of the bridge member 136, which rest on the forehead of the user. The cushion 140 might be constructed of silicon or any foam materials as is known in the art for providing cushioning. The cushions lock into slots 137 in the T-Section 142

In a further embodiment the forehead rest 106 described previously may include a weakened section at its base which allows the joining member to pivot from the hollow body. The extent of flexibility of this joint can be varied by its thickness to any desired strength. The bridge member extends up to the forehead of the user. In a further alternative the mask may include a vertical upwardly extending inlet. In this case the member is hinged at its base to either side of the inlet passage. Again the member would then extend to the forehead.

Figure 8:
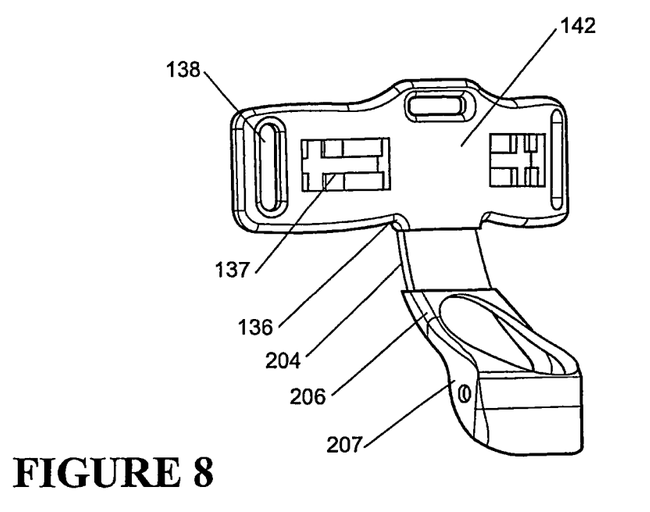
FIG. 8 is a perspective view of the forehead rest in isolation.

Particularly referring to FIGS. 7 and 8 the forehead rest 106 is shown including a flexible or malleable insert 204. The preferred embodiment the malleable insert 204 comprises a metal strip joining the hollow body 102 to the forehead rest 106. The metal can be chosen from anyone of a number of metals known in the art to provide enough malleability to be bend to a particular angle and enough stiffness to retain the angle once installed on the patient. Stiffness can be configured by choice and thickness of insert 204. An example is 1 mm thickness. The malleable insert 204 maybe connected to the hollow body 102 by mounting 206.

Mounting 206 may include additional pivot (207, FIG. 8) or adjustment mechanisms. Additionally forehead rest 106, insert 204 and/or body 102 may be integral or encapsulated. Preferably insert 204 is supported within a mould during fabrication. Polycarbonate or other suitable plastics are preferably injection moulded to encapsulate each end of the insert, into the body 102 and the forehead rest 106 respectively. Preferably the insert 104 displays a limited degree of work hardening over the range of plastic deformation. For example soft alloys are less likely to snap after a large amount of bending back and forwards. Alloys involving aluminium or copper are possible constructions. Portions of the insert, body and/or forehead rest may be encapsulated by a pliable material eg silicone.

The invention claimed is:

1. A device for delivering gases to a user comprising:
   a mask, in use in fluid communication with a supply of gases, said mask configured to in use substantially seal against the face of the user without substantial pressure thereto and deliver said gases to a nasal cavity or oral cavity or both of the user, said mask being made of a plastic material;
   a forehead support adapted to in use rest on the forehead of the user, said forehead support being made of a plastic material and comprising slots configured to receive headgear straps; and
   an attachment extending between said mask and said forehead support, said attachment being configured to allow adjustment of said forehead support with respect to said mask toward and away from the forehead of the user under in use conditions while restricting lateral movement of said forehead support relative to said mask along the forehead of the user, wherein a first end of said attachment is encapsulated in the plastic material of said mask via injection molding to couple to said mask, an opposite second end of said attachment is encapsulated in said forehead support via injection molding of the plastic material of said forehead support, and a portion of said attachment between the first end and the opposite second end is not encapsulated in said forehead support or the plastic material of said mask;
   said attachment being malleable such that said forehead support may be configured to a certain angle relative to said mask and being configured to retain said certain angle in use when said device is in use.

2. A device as claimed in claim 1, the mask further comprising a main body and a mounting, the mounting pivotally coupled to the main body and configured to connect the attachment to the main body of the mask, wherein the first end of the attachment is encapsulated in the mounting.

3. A device as claimed in claim 1, wherein said attachment comprises a metal strip at least in part encapsulated by a pliable material.

4. A device as claimed in claim 1, wherein said attachment comprises a metal strip.

5. A device as claimed in claim 1, wherein said attachment is the only connection between said mask and said forehead support.

6. A respiratory system user interface comprising:
   a mask configured to in use substantially seal against the face of a user, the mask comprising a mask body;
   a forehead support adapted to in use rest on a forehead of the user, the forehead support formed as a separate structure from the mask and comprising slots configured to receive headgear straps; and
   a malleable insert extending between and coupling the forehead support and the mask, a first end of the malleable insert being encapsulated in a first plastic portion configured to couple the first end of the malleable insert to the mask body, an opposite second end of the malleable insert being encapsulated in a second plastic portion configured to couple the second end of the malleable insert to the forehead support, a portion of the malleable insert between the first end and the second end that is not encapsulated in the first plastic portion or the second plastic portion, the malleable insert configured to allow anterior and posterior adjustment of the forehead support relative to the mask and the forehead of the user under in use conditions and configured to retain a desired adjustment position, the malleable insert configured to restrain lateral movement of the forehead support relative to the forehead of the user.

7. A device as claimed in claim 6, wherein the malleable insert is the only connection between an upper end of the mask and a lower end of the forehead support.

8. A device as claimed in claim 6, wherein said malleable insert comprises a metal strip.

9. A respiratory system interface as claimed in claim 6 wherein the malleable insert is coated with a soft pliable material.

10. A respiratory system interface as claimed in claim 6 wherein the mask body has a triangular cavity for receiving an inner cushion.

11. A respiratory system interface as claimed in claim 6 further comprising a pivot configured to provide pivotal adjustment of the forehead support relative to the mask, the pivotal adjustment being in addition to the anterior and posterior adjustment provided by the malleable insert.

12. A respiratory system interface as claimed in claim 6 wherein the malleable insert has a thickness of about 1 mm.

13. A respiratory system interface as claimed in claim 6 wherein the first plastic portion is a mounting coupled to the mask body.

14. A respiratory system interface as claimed in claim 13 wherein the mounting includes a pivot or adjustment mechanism.

15. A respiratory system interface as claimed in claim 6 wherein the malleable insert is formed of aluminum or copper.

16. A respiratory system interface as claimed in claim 6 wherein the first plastic portion is polycarbonate and the second plastic portion is polycarbonate.

17. A respiratory system interface as claimed in claim 6 wherein the malleable insert has a rectangular cross-section.

18. A respiratory system interface as claimed in claim 6 wherein the second plastic portion is a portion of the forehead support such that the malleable insert is directly attached to the forehead support.

19. A respiratory system interface as claimed in claim 6 wherein the malleable insert is independent from an inspiratory conduit for receiving gases.

20. A respiratory system interface as claimed in claim 6 wherein the mask comprises an inner cushion and an outer sheath.

21. A respiratory system interface as claimed in claim 20 wherein the outer sheath loosely covers the inner cushion.

\* \* \* \* \*

UNITED STATES PATENT AND TRADEMARK OFFICE
CERTIFICATE OF CORRECTION

PATENT NO. : 10,463,828 B2  
APPLICATION NO. : 10/487518  
DATED : November 5, 2019  
INVENTOR(S) : Lewis George Gradon et al.

Page 1 of 1

It is certified that error appears in the above-identified patent and that said Letters Patent is hereby corrected as shown below:

In the Specification

In Column 5, Line 21, delete "eg" and insert --e.g.,--.

In the Claims

In Column 6, Line 26, Claim 7, delete "device" and insert --respiratory system--.

In Column 6, Line 29, Claim 8, delete "device" and insert --respiratory system--.

Signed and Sealed this  
Eighteenth Day of February, 2020

Andrei Iancu  
*Director of the United States Patent and Trademark Office*